United States Patent
Antonio et al.

(10) Patent No.: US 10,036,762 B2
(45) Date of Patent: Jul. 31, 2018

(54) METHOD FOR DETERMINING THE POSITION OF A FIXED CARTOGRAPHY TOKEN INCLUDING DEDUCING COORDINATE POINTS OF THE CARTOGRAPHY TOKEN WITH RESPECT TO MOVEMENT OF A NEEDLE

(71) Applicant: DIAGNOSTICA STAGO, Asnieres-sur-Seine (FR)

(72) Inventors: Pascal Antonio, Juziers (FR); Olivier Cochelin, Saint Gratien (FR); Cyril Greffier, Houilles (FR)

(73) Assignee: DIAGNOSTICA STAGO, Asnieres-sur-Seine (FR)

( * ) Notice: Subject to any disclaimer, the term of this patent is extended or adjusted under 35 U.S.C. 154(b) by 58 days.

(21) Appl. No.: 15/103,197

(22) PCT Filed: Dec. 9, 2014

(86) PCT No.: PCT/FR2014/053222
§ 371 (c)(1),
(2) Date: Jun. 9, 2016

(87) PCT Pub. No.: WO2015/086977
PCT Pub. Date: Jun. 18, 2015

(65) Prior Publication Data
US 2016/0320424 A1    Nov. 3, 2016

(30) Foreign Application Priority Data
Dec. 12, 2013    (FR) ...................................... 13 62493

(51) Int. Cl.
*G01N 35/10*    (2006.01)

(52) U.S. Cl.
CPC .............................. *G01N 35/1011* (2013.01)

(58) Field of Classification Search
CPC ........... G01N 35/1011; G01N 35/1074; G01N 2035/0494; G01N 2035/1013;
(Continued)

(56) References Cited

U.S. PATENT DOCUMENTS

| 5,443,792 A | 8/1995 | Buhler |
| 5,529,754 A | 6/1996 | Bonacina et al. |

(Continued)

FOREIGN PATENT DOCUMENTS

| EP | 1 354 185 A1 | 10/2003 |
| FR | 2 764 703 A1 | 12/1998 |

(Continued)

OTHER PUBLICATIONS

International Search Report, dated Mar. 4, 2015, from corresponding PCT Application.

*Primary Examiner* — Harshad R Patel
*Assistant Examiner* — Brandi Hopkins
(74) *Attorney, Agent, or Firm* — Young & Thompson (57) ABSTRACT

A method of determining the position of at least one fixed cartography token (10) of an automaton, the token (10) including a base (11) having a lateral surface and an end face (14a), a stud (15) of smaller cross section than the base (11) projecting from the end face (14a) of the base (11), the stud (15) including an end face (16) opposite the base (11). The method is aimed in particular at deducing the coordinates (XO, YO, ZO) of at least one point (O) of the cartography token (10) with respect to a movable member.

16 Claims, 4 Drawing Sheets

(58) Field of Classification Search
CPC ............. G01N 35/109; G01N 35/1004; G01N 35/1095; G01N 35/02; G01B 7/023; G01B 7/003; B25J 9/1692; Y10T 436/114998

See application file for complete search history.

(56) References Cited

U.S. PATENT DOCUMENTS

| | | |
|---|---|---|
| 6,355,488 B1 | 3/2002 | Rousseau et al. |
| 2007/0065945 A1 | 3/2007 | Sigrist |
| 2011/0306032 A1* | 12/2011 | Galiano ............... G01N 35/028 435/3 |
| 2012/0065912 A1 | 3/2012 | Corkan et al. |

FOREIGN PATENT DOCUMENTS

| | | |
|---|---|---|
| WO | 02/059570 A1 | 8/2002 |
| WO | 2005/059568 A1 | 6/2005 |
| WO | 2012/129105 A1 | 9/2012 |

\* cited by examiner

METHOD FOR DETERMINING THE POSITION OF A FIXED CARTOGRAPHY TOKEN INCLUDING DEDUCING COORDINATE POINTS OF THE CARTOGRAPHY TOKEN WITH RESPECT TO MOVEMENT OF A NEEDLE

BACKGROUND OF THE INVENTION

The present invention relates to a method for determining the position of at least one fixed cartography token of an automaton. The invention applies in particular to automated in-vitro diagnosis devices, in particular in the field of haemostasis.

Such a device or automaton comprises a fixed frame on which plates are fixed, comprising housings for positioning containers in the form of bottles, tubes or reaction bowls. The device comprises, for example, a plate intended to support bottles containing reactive products, a plate intended to support tubes containing plasma samples, and a plate intended to support reaction bowls in which measurements are made.

The device further comprises one or more motorised arms each comprising a head able to move according to cartesian coordinates (X, Y, Z) or cylindrical coordinates (θ, r, Z) and equipped with a pipette/needle assembly or a gripping system for moving the bowl from one station to another.

Part of such an automaton is for example known from the document FR 2 764 703 in the name of the applicant.

The needle (or pipette) is conventionally equipped with capacitive detection means, making it possible in particular to detect the position as from which the needle comes into contact with the liquid. Such detection means are generally referred to by the English acronym LLD (standing for liquid level detection).

In general terms, it is necessary to precisely control the position of the end of each needle with respect to the various containers, so as to avoid the needle striking the edge or bottom of a container, which may cause breakage or deformation of the needle, or damage to the container causing contamination of the reactive product or of the sample to be analysed.

However, producing such a device necessarily gives rise to uncertainties in positioning, due for example to the method of manufacturing each part of the device (manufacturing tolerances, etc), to the method of assembling the various parts with respect to one another (assembly clearances, imprecision during assembly, etc), or to the method of moving the arm equipped with the movable head on which the needle is mounted (control by means of stepping motors for example).

There therefore exists a need to precisely determine the positions of the various containers fixed with respect to the movable needle.

For this purpose, the patent EP 1 354 185 proposes using cartography tokens, the positions of which with respect to the containers are known. Each token has a roughly cylindrical shape, the top end of which comprises a blind hole. Pipettes or needles are mounted on a movable head actuated by an arm that can be moved along X, Y and Z orthogonal to one another. The needles are in particular brought into contact with the internal surface of the blind hole, so as to precisely determine the positions of the cartography tokens fixed with respect to the movable needles.

During such a method, the reactive products or the samples contained in some needles may soil the blind holes and may cause contamination of the other needles. In order to avoid this, it is necessary to clean the cartography tokens, which is relatively tedious when they comprise blind holes with a diameter slightly greater than the needle.

SUMMARY OF THE INVENTION

The aim of the invention is in particular to afford a simple, effective and economical solution to the aforementioned problems.

To this end, it proposes a method for the automatic determination of the position of at least one fixed cartography token of an automaton, said token comprising a base comprising a lateral surface and an end face, a stud with a smaller cross-section than the base projecting from the end face of the base, said stud comprising an end face opposite to the base, said method comprising the steps consisting of:

(a) Moving a movable member until it is in contact with a first zone of the lateral surface of the base, (b) Moving the movable member until it is in contact with a second zone of the lateral surface of the base, (c) Moving the movable member until it is in contact with the end face of the stud, (d) Moving the movable member until it is in contact with the end face of the base, (e) Deducing therefrom the coordinates of at least one point on the cartography token with respect to the movable member.

The use of at least one cartography token makes it possible to determine, with great precision, the position of elements of the automaton situated in the vicinity of the cartography token and the positions of which with respect to said token are referenced. Thus, if containers (bottles, tubes, bowls) are situated in the vicinity of such a cartography token, it is possible to determine their exact positions by means of the method according to the invention.

Steps (a) and (b) make it possible for example to determine the position of a point on the token with respect to the movable member, along X and Y axes (in a system of coordinates of the cartesian type) or the polar coordinates θ, r (in a system of coordinates of the cylindrical type), step (c) making it possible to determine the position along Z of the aforementioned point on the token with respect to the movable member.

Step (d) makes it possible to check that the determined coordinates X, Y or θ, r of the point on the token are correct. This step can also make it possible to validate the coordinate Z of the point on the token.

Since the cartography token has no blind hole, it does not risk retaining any drops of liquid. The risks of contamination are therefore limited. Such a token can also be cleaned easily. Moreover, the stud situated projecting at the top of the token, the cross-section of which is close to that of the needle, makes it possible to visually and very easily check the correct alignment of the needle with the token.

Advantageously, the base has a parallelepipedal form comprising two first opposite lateral faces extending parallel to a first plane defined by an X axis and a Z axis, two second opposite lateral faces extending substantially parallel to a second plane defined by an X axis and a Z axis, two opposite end faces extending substantially parallel to a third plane defined by the X axis and the Y axis, the X, Y and Z axes being orthogonal to one another, the end face of the stud being substantially parallel to the third plane.

The X and Y axes are for example disposed horizontally and the Z axis is for example disposed vertically.

In this case, the method may comprise the steps consisting of:

positioning the movable member opposite one of the first lateral faces of the base, moving the movable member along the X axis, until it is in contact with the corresponding first lateral face, deducing therefrom a coordinate along the X axis, of at least one point on the cartography token with respect to the movable member, positioning the movable member opposite one of the second lateral faces of the base, moving the movable member along the Y axis until it is in contact with the corresponding second lateral face, deducing therefrom a coordinate along the X axis, of at least one point on the cartography token with respect to the movable member, positioning the movable member opposite the end face of the stud, moving the movable member along the Z axis until it is in contact with the end face of the stud, deducing therefrom a coordinate along the Z axis, of at least one point on the cartography token with respect to the movable member.

Preferably, after contact of the movable member with the end face of the stud, the movable member is positioned opposite the end face of the base and is then moved along the Z axis until it is in contact with the end face of the base.

If the contact with the end face of the base is detected, then it is guaranteed that the coordinates along X and Y of the aforementioned point on the token are correctly determined.

Furthermore, the method may comprise at least one step of searching for the cartography token consisting of moving the movable member so as to sweep at least one given zone on a given path, until it is in contact with the lateral surface of the base, the position of the movable member along the longitudinal axis of the token (Z axis) remaining unchanged during the search step.

As indicated previously, before having performed the method according to the invention, the position of the movable member with respect to the cartography token is known with an uncertainty that mainly depends on the method of manufacturing the parts and the method of connecting the parts together. This uncertainty region is for example of around 5 mm on each of the X, Y and Z axes, when reasoning in cartesian coordinates. If the cross-section of the cartography token in the plane X-Y (that is to say in the plane divided by the X and Y axes) is greater than the uncertainty region in this same plane, then moving the movable member along X or along Y makes it possible to ensure contact between the movable member and the corresponding lateral face of the base of the token at the moment when the movable member is brought opposite the corresponding lateral face and the movable member is next moved along the X or Y axis.

Conversely, if the cross-section of the cartography token in the plane X-Y is smaller than the region of uncertainty in this same plane, then it is not certain that the movable member encounters the corresponding lateral face of the base of the token. In this case, the aforementioned search step may be made necessary.

In such a case, said path of the movable member during the search step may have the form of a spiral or comprise a succession of lines oriented in the same direction and each passing through the given zone to be swept, said lines being offset from one another.

Furthermore, if the movable member has not come into contact with the lateral surface of the base of the cartography token during a search step, then another search step is performed, at a different position of the movable member along the longitudinal axis of the token.

Such a case may for example arise when the chosen height (that is to say the position along Z in the aforementioned case) for the search step is wrongly or erroneously chosen, because in particular of the uncertainties along the Z axis.

In this case, a plurality of search steps are performed, for various heights, until the movable member encounters one of the lateral faces of the base of the cartography token.

The contact between the movable member and the base or the stud of the token can be detected by capacitive measurement. In the case of an in-vitro diagnosis automaton for example, such measuring means are already integrated in the existing needles or pipettes. It is therefore not necessary to add additional measuring means thereto.

The automaton may comprise at least one zone equipped with fixed elements, such as for example specimens, bowls or bottles, said zone comprising at least three cartography tokens, the positions of at least one point on each cartography token being determined with respect to the movable member by means of the aforementioned steps (a) to (e), the positions of the various fixed elements of the zone being determined by interpolation using the positions of the points on the various cartography tokens.

The positions of the three (at a minimum) cartography tokens, that is to say of the three corresponding points, makes it possible to define a plane. This plane is divided into a plurality of sectors organised like a matrix. The actual position of each sector is then determined with respect to the coordinates of the points on the cartography tokens. Each fixed element can be associated with a sector so that it is possible to determine the actual position of each fixed element with respect to the movable member. It is also possible to associate a plurality of fixed elements with the same sector.

In this case, the zone may comprise a plate extending in a plane, housings being provided in said plate, the fixed elements being mounted in said housings.

Preferably, the automaton is an in-vitro diagnosis apparatus, the movable member being a sampling needle or pipette.

The invention also concerns a cartography token for implementing the aforementioned method, characterised in that it comprises a base comprising a lateral surface and an end face, a stud with a smaller cross-section than the base projecting from the end face of the base, said stud comprising an end face opposite to the base. Preferably, the base and/or the stud are parallelepipedal in shape.

BRIEF DESCRIPTION OF THE DRAWINGS

The invention will be understood better and other details, features and advantages of the invention will emerge from a reading of the following description given by way of non-limitative example with reference to the accompanying drawings, in which.

DETAILED DESCRIPTION OF THE PREFERRED EMBODIMENTS

Figure 1:
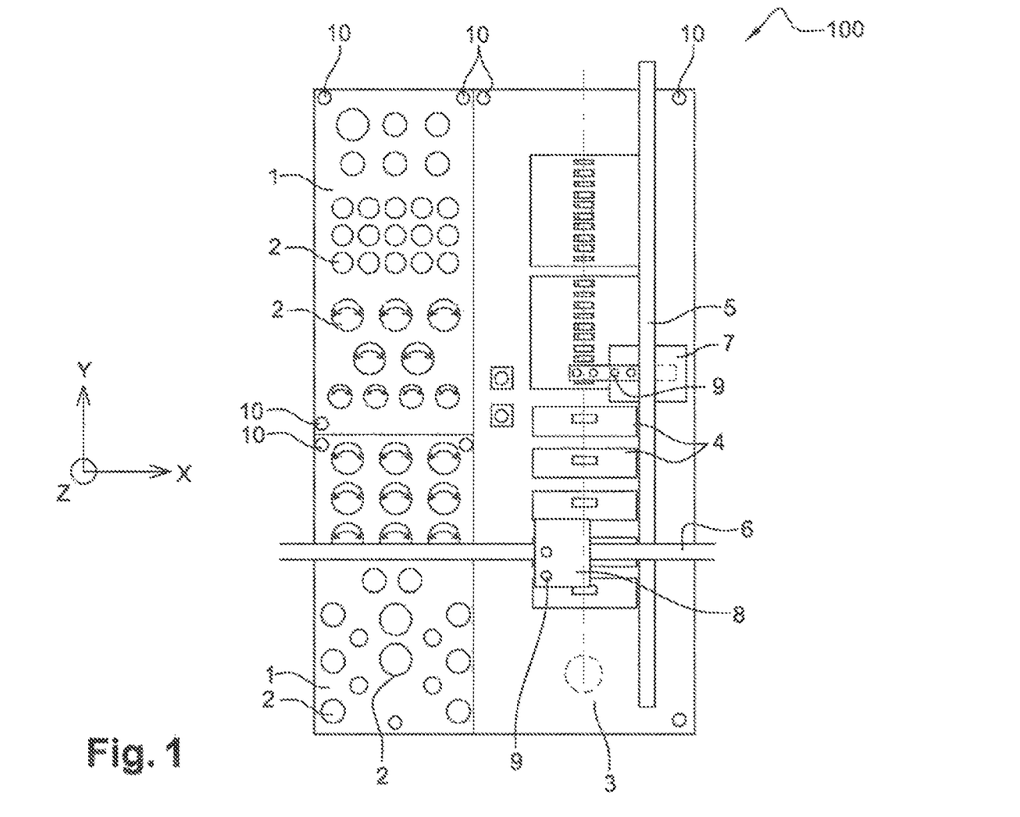
FIG. 1 is a plan view of part of an in-vitro diagnosis automaton comprising cartography tokens according to the invention.

FIG. 1 illustrates part of an automated in-vitro diagnosis device 100, in particular in the field of haemostasis.

Such a device or automaton comprises a fixed frame on which plates are fixed, comprising housings in which containers are mounted, for example in the form of bottles, tubes or reaction bowls. The device comprises for example one or more plates 1 intended to support bottles 2 containing reactive products, a plate (not shown) intended to support tubes containing plasma samples, and a plate 3 intended to support reaction bowls 4 in which measurements are made.

The device further comprises at least one motorised arm 5, 6 comprising a head 7, 8 able to move along cartesian coordinates (X, Y, Z) or cylindrical coordinates (θ, r, Z) and equipped with one or more needles 9. In the remainder of the description, cartesian coordinates will be used to illustrate the invention, although it is also possible to use cylindrical coordinates.

The needles 9 are equipped with capacitive detection means (or any other means for detecting the absence of a needle), making it possible in particular to detect the position as from which the needle 9 comes into contact with the liquid. Such detection means are generally referred to by the English acronym LLD (standing for liquid level detection). Such means also make it possible to detect contact between the needle 9 and metal cartography tokens 10 mounted fixedly on the plates 1, 3 and therefore fixed in space.

Figure 2:
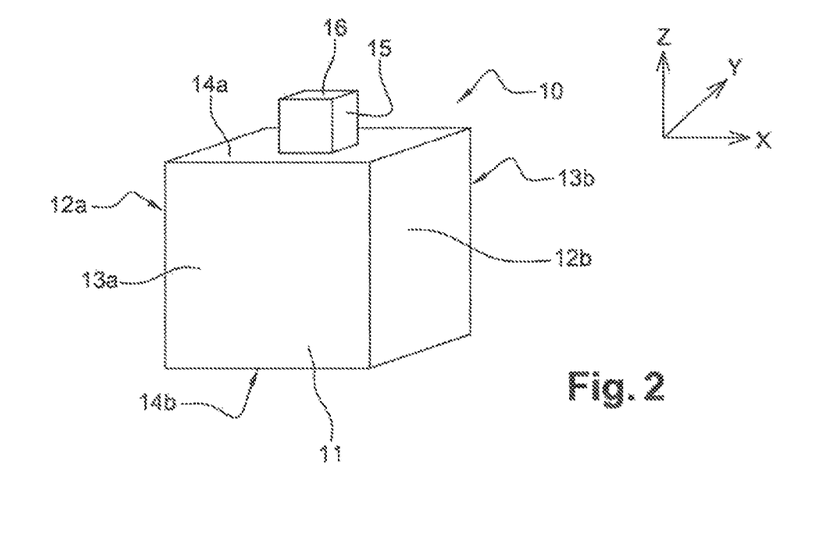
FIG. 2 is a perspective view of an embodiment of a cartography token according to the invention.

As is more clearly visible in FIG. 2, each cartography token 10 comprises a base 11 in the form of a cube, comprising two opposite and roughly vertical faces 12a, 12b, oriented substantially parallel to the plane YZ, two opposite and roughly vertical faces 13a, 13b oriented substantially parallel to the plane X and Z, and two opposite and roughly horizontal faces 14a, 14b oriented substantially parallel to the plane XY. The planes YZ, XZ and XY are defined respectively by the axes Y and Z, by the axes X and Z and by the axes X and Y.

The face 14a is surmounted by a stud 15 in the form of a cube, with a smaller cross-section than the base 11 in the plane XY and positioned at the centre of the face 14a. The faces of the stud 15 are substantially parallel to the corresponding faces of the base 11.

Naturally it is possible to use cartography tokens 10 having other forms. The base 11 and/or the stud 15 may for example be cylindrical.

Each plate 1, 3 or each part of the plate 1, 3 is for example equipped with three cartography tokens 10, for the reasons detailed below.

As indicated previously, producing such an automaton necessarily gives rise to uncertainties, due for example to the method of manufacturing each part of the automaton (manufacturing tolerances, etc.), to the method of assembling the various parts with respect to one another (assembly clearances, imprecision during manual assembly for example), or to the method of moving the arms 5, 6 equipped with movable heads 7, 8 on which the needles 9 are mounted (control by means of stepping motors, for example).

However, it is necessary to precisely control the position of the end of each needle 9 with respect to the various containers 2, 4 (bottles, tubes, bowls) so as to prevent the needle 9 striking the edge of a container 2, 4, which may cause breakage or deformation of the needle 9, or damage to the container 2, 4, causing contamination of the reactive product or of the sample to be analysed.

The invention proposes for this purpose to determine precisely the coordinates of at least one point on each cartography token 10 of the automaton, with a view to deducing therefrom the precise positions of each container 2, 4, the positions of the containers 2, 4 being known and referenced with respect to the cartography tokens 10.

Figure 3:
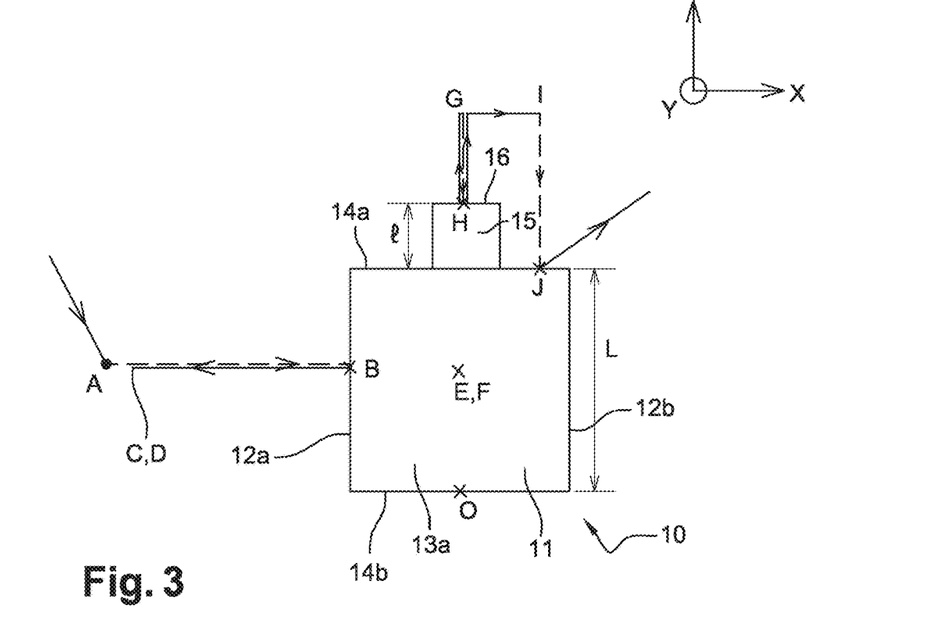
FIGS. 3 and 4 are schematic views, respectively front and plan views, illustrating the cartography token and the various successive steps of the method according to the invention.
Figure 4:
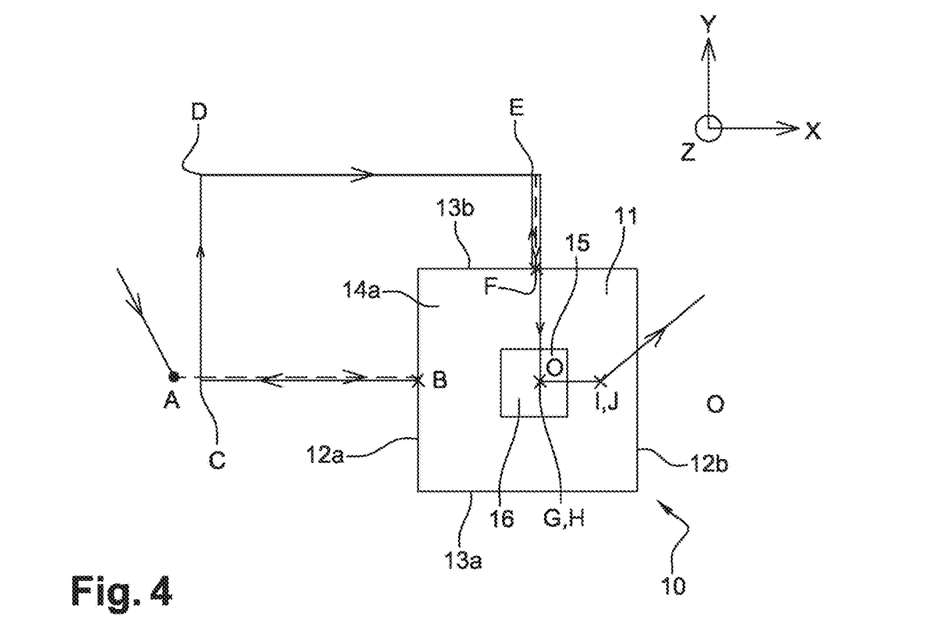

FIGS. 3 and 4 illustrate a method for determining the position of a cartography token 10, in accordance with one embodiment of the invention. The path of the end of a movable needle 9 and of a cartography token 10 are illustrated in these figures.

The centre of the face 14b is defined by O, the point O having the coordinates XO, YO, ZO. The base 11 has a width denoted L and the stud 15 has a width denoted 1.

The method according to the invention comprises the following successive steps.

First of all, the needle 9 is brought close to the token 10 by a rapid movement as far as a point A. The high-speed movements are illustrated here in bold lines. The point A is situated outside the uncertainty zone. The uncertainty zone is the zone in which the token 10 may potentially be situated, having regard to all the estimated uncertainties due to the manufacturing tolerance, the assembly clearances, etc. It is thus guaranteed that the needle 9 does not strike the token 10 while moving at high speed towards the point A.

The point A is situated opposite (along the X axis) the estimated position of the centre of the face 12a of the base 11 of the token 10.

The needle 9 is next moved at low speed (which is shown in broken lines) along the X axis and in the positive direction of this axis. Such a movement is denoted +X by convention. This movement is continued until contact between the needle 9 and the base 11 is detected. The contact point is referenced B.

The coordinate XB of the point B is then determined and it is possible to calculate the coordinate XO of the token 10 in accordance with the formula XO=XB+0.5 L.

The needle 9 is next moved quickly away from the token 10 in a movement −X (that is to say along the X axis and in the negative direction), by an amount corresponding for example to the width L of the base 11, until it reaches the point C.

The needle 9 then undergoes a rapid movement along +Y, for example by an amount L, as far as the point D, and then a rapid movement along +X, for example by an amount 1.5 L, as far as the point E. The point E is then situated opposite the face 13b of the base 11. The needle 9 is next moved along −Y at low speed, until contact between the needle 9 and the base 11 on the face 13b is detected at the point F.

The coordinate YF of the point F is then determined and it is possible to calculate the coordinate YO of the token 10 in accordance with the formula YO=YF−0.5 L. The needle 9 is then moved quickly away from the token 10 along +Y, so as to return to the point E for example.

The end of the needle 9 is then brought quickly to the point G opposite the centre of the face 16 of the stud 15 along the Z axis. The face 16 is opposite to the face 14a of the base 11 and parallel to this face 14a. Because of the structure of the token 10, the centre of the face 16 has the coordinates XO, YO in the plane XY, these coordinates having been determined previously. The position along Z of the point G and the path between the points E and G make it possible to avoid a collision between the needle 9 and the token 10.

The needle 9 is next moved at low speed along −Z, until it comes into contact at the point H with the face 16 of the stud 15. The coordinate ZH of the point H is then determined and it is possible to calculate the coordinate ZO of the token 10 in accordance with the formula ZO=ZF−(L+1).

The end of the needle 9 is next offset laterally (that is to say along X and/or along Y) so as to be situated opposite the face 14a of the base 11 (point I). The needle 9 is then moved at low speed along −Z until it comes into contact with said face 14a (point J). If the coordinate ZJ satisfies for example the equation ZJ=ZH−1, then it is possible to guarantee that the coordinates XO, YO and ZO are correct.

The needle 9 can next be moved quickly away from the token 10 and be directed towards the following cartography token 10 for example.

This method can be repeated for each cartography token 10 so as to determine, for each token 10, the coordinates XO, YO, ZO of the reference point O of the tokens 10.

Figure 5:
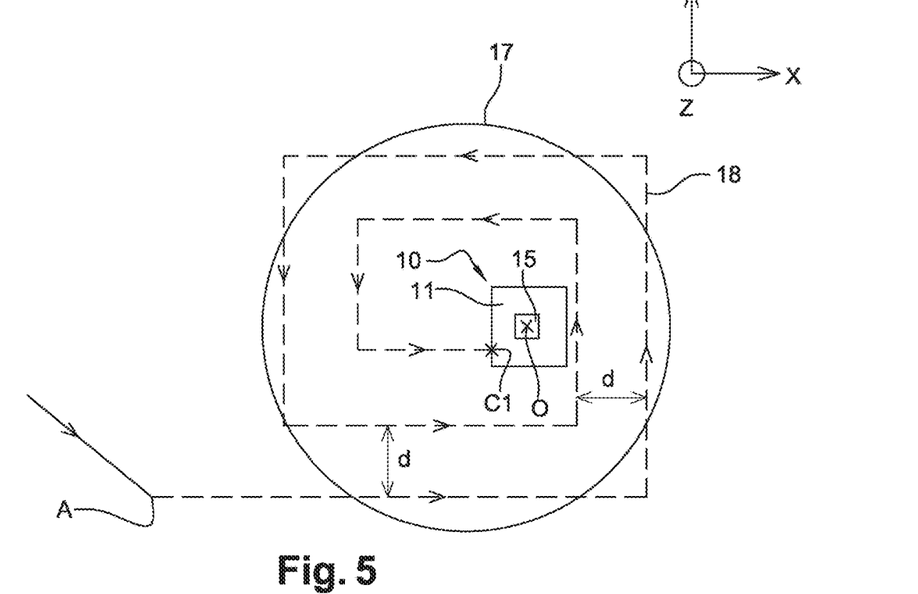
FIG. 5 is a schematic plan view, illustrating the cartography token and a search step according to the invention.

FIG. 5 illustrates the case where the uncertainty zone 17 is greater than the dimensions of the token 10. In this case there exists a risk that the needle 9 does not encounter the face 12a of the token 10 when it moves from the point A (no detection of the point B). In this case, a step of seeking the cartography token 10 is proceeded with, consisting of moving the end of the needle 9 so as to sweep a given zone along a defined path 18, until said end is in contact with one of the lateral faces 12a, 12b, 13a, 13b of the base 11, the position of said end along the Z axis remaining unchanged during this search step.

In the case depicted in FIG. 5, the path 18 has spiral form, or more particularly a "square" spiral form defined by a succession of lines oriented alternately along the X axis and along the Y axis, the lines making up this spiral 18 being separated from one another by an amount d that is a function of the width L of the base 11 for example.

Figure 6:
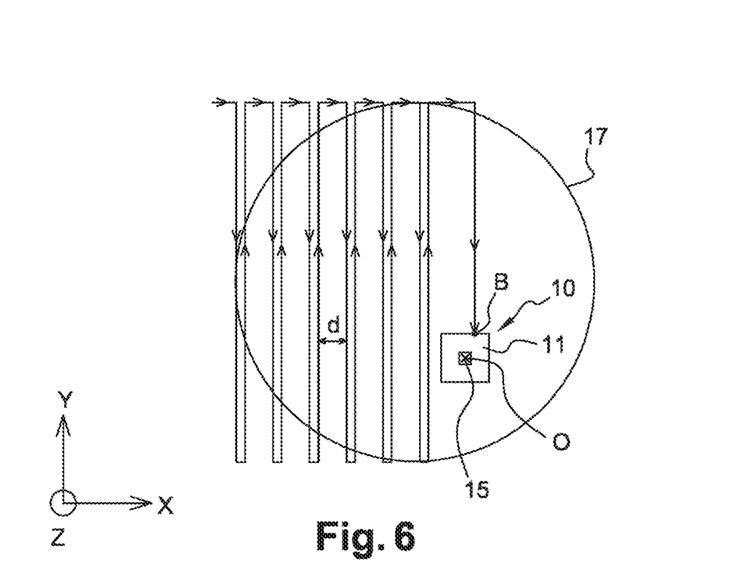
FIG. 6 is a view corresponding to FIG. 5, illustrating a variant embodiment of the invention.

FIG. 6 illustrates a variant embodiment that differs from the one disclosed with reference to FIG. 5 in that the path 18 has a so-called comb shape and comprises a succession of lines oriented in the same direction, here the direction Y, and each passing through the uncertainty zone 17 in the aforementioned direction Y, said lines being offset from one another along the X axis, by an amount d that is a function of the width L of the base 11, for example.

If, during such a search step, the end of the needle 9 has not encountered the token 10, then it is that this end is situated at a coordinate along Z that is greater than the coordinate along Z of the face 16 or than the face 14a of the token 10.

In such a case, the end of the needle 9 is once again positioned outside the uncertainty zone 17, and then this end is moved along −Z, by an amount that is for example a function of the width L of the base 11. A new search step can then begin. This procedure is followed until contact is established between the needle 9 and the token 10. Once contact is established (detection of the point B), it is possible to continue the various steps of the method detailed above (from the point B).

As indicated previously, each plate 1, 3 or each part of the plate 1, 3 comprises three tokens 10 (at a minimum) fixed with respect to said plates 1, 3. The method described previously makes it possible to precisely determine the coordinates XO, YO, ZO of at least one point O of each token 10. Each plate 1, 3 comprises housings in which containers 2, 4 are mounted, the positions of the housings (and therefore of the containers) being known and referenced with respect to the aforementioned points O.

The determination of the various points O makes it possible correct for example any lack of horizontality, that is say the angle α (FIG. 7), with respect to the plane XY, or the bending or twisting of each plate 1, 3 or of each zone of the plate 1, 3, and next to calculate, by interpolation, the exact (or almost exact) coordinates of at least one point C on each container 2, 4. The point C is for example the centre of the opening of the corresponding container 2, 4.

Figure 7:
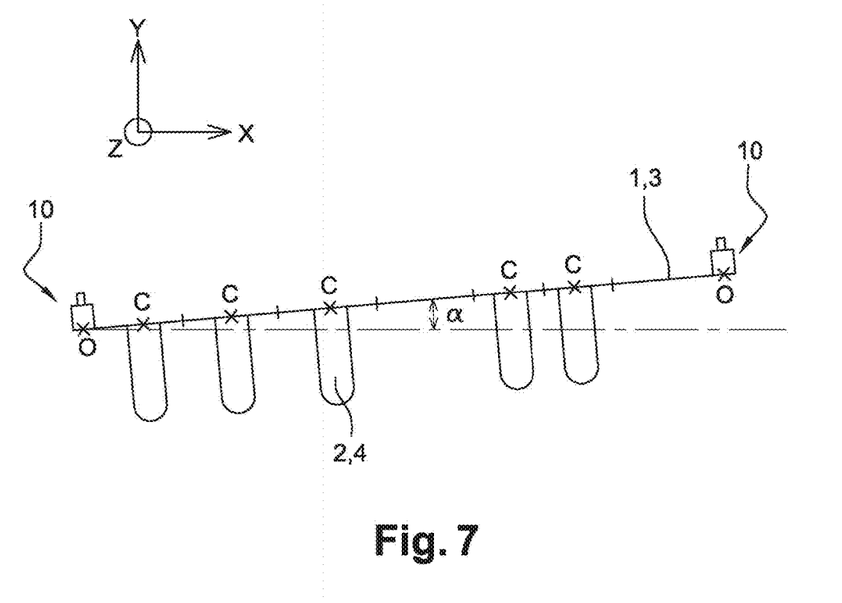
FIG. 7 is a schematic side view illustrating a plate on which cartography tokens and tubes are mounted.

Once the coordinates of the point C of the containers 2, 4 are established precisely, it is then possible to move the needles 9 with certainty, without risk of collision with the plates 1, 3 or with the containers 2, 4.

The invention claimed is:

1. A method for determining the position of at least one fixed cartography token (10) of an automaton, where said token (10) includes a base (11) comprised of a lateral surface and an end face (14a), and a stud (15) with a smaller cross-section than the base (11) projecting from the end face (14a) of the base (11), said stud (15) having an end face (16) opposite to the base (11), said method comprising the steps of:
   (a) moving a movable member (9) until the movable member (9) is in contact with a first zone (12a) of the lateral surface of the base (11),
   (b) moving the movable member (9) until the movable member (9) is in contact with a second zone (13b) of the lateral surface of the base (11),
   (c) moving the movable member (9) until the movable member (9) is in contact with the end face (16) of the stud (15),
   (d) moving the movable member (9) until the movable member (9) is in contact with the end face (14a) of the base (11),
   (e) deducing therefrom the coordinates (XO, YO, ZO) of at least one point (O) on the cartography token (10) with respect to the movable member (9).

2. The method according to claim 1, wherein use is made of the token, the base (11) of which has a parallelepiped form comprising two first opposite lateral faces (12a, 12b) extending parallel to a first plane (YZ) defined by a Y axis and a Z axis, two second opposite lateral faces (13a, 13b) extending parallel to a second plane (XZ) defined by an X axis and a Z axis, two opposite end faces (14a, 14b) extending parallel to a third plane (XY) defined by the X axis and the Y axis, the X, Y and Z axes being orthogonal to one another, the end face (16) of the stud being parallel to the third plane (XY).

3. The method according to claim 2, further comprising the steps of:
   positioning the movable member (9) opposite one (12a) of the first lateral faces (12a, 12b) of the base (11),
   moving the movable member (9) along the X axis, until the movable member (9) is in contact with the corresponding first lateral face (12a),
   deducing therefrom a coordinate (XO) along the X axis, of at least one point (O) on the cartography token (10) with respect to the movable member (9),
   positioning the movable member (9) opposite one of the second lateral faces (13a, 13b) of the base (11),
   moving the movable member (9) along the Y axis until the movable member (9) is in contact with the corresponding second lateral face (13b),
   deducing therefrom a coordinate (YO) along the X axis, of at least one point (O) on the cartography token (10) with respect to the movable member (9), positioning the movable member (9) opposite the end face (16) of the stud (15), moving the movable member (9) along the Z axis until the movable member (9) is in contact with the end face (16) of the stud (15), deducing therefrom a coordinate (ZO) along the Z axis, of at least one point (O) on the cartography token (10) with respect to the movable member (9).

4. The method according to claim 3, wherein, after contact of the movable member (9) with the end face (16) of the stud (15), the movable member (9) is positioned opposite the end face (14a) of the base (11) and is then moved along the Z axis until the movable member (9) is in contact with the end face (14a) of the base (11).

5. The method according to claim 4, further comprising:
at least one step of searching for the cartography token (10) consisting of moving the movable member (9) so as to sweep a given zone (17) along a defined path (18), until the movable member (9) is in contact with the lateral surface (12a, 12b, 13a, 13b) of the base (11), the position of the movable member (9) along a longitudinal axis (Z) of the token (10) remaining unchanged during the search step.

6. The method according to claim 3, further comprising:
at least one step of searching for the cartography token (10) consisting of moving the movable member (9) so as to sweep a given zone (17) along a defined path (18), until the movable member (9) is in contact with the lateral surface (12a, 12b, 13a, 13b) of the base (11), the position of the movable member (9) along a longitudinal axis (Z) of the token (10) remaining unchanged during the search step.

7. The method according to claim 2, further comprising:
at least one step of searching for the cartography token (10) consisting of moving the movable member (9) so as to sweep a given zone (17) along a defined path (18), until the movable member (9) is in contact with the lateral surface (12a, 12b, 13a, 13b) of the base (11), the position of the movable member (9) along a longitudinal axis (Z) of the token (10) remaining unchanged during the search step.

8. The method according to claim 2, wherein the contact between the movable member (9) and the base (11) or the stud (15) of the token (10) is detected by capacitive measurement.

9. The method according to claim 1, further comprising:
at least one step of searching for the cartography token (10) consisting of moving the movable member (9) so as to sweep a given zone (17) along a defined path (18), until the movable member (9) is in contact with the lateral surface (12a, 12b, 13a, 13b) of the base (11), the position of the movable member (9) along a longitudinal axis (Z) of the token (10) remaining unchanged during the search step.

10. The method according to claim 9, wherein said path (18) of the movable member (9) during the search step has a spiral shape or comprises a succession of lines oriented in the same direction and each passing through the given zone to be swept, said lines being offset with respect to one another.

11. The method according to claim 10 wherein, the movable member (9) not having come into contact with the lateral surface (12a, 12b, 13a, 13b) of the base (11) of the cartography token (10) during a search step, then another search step is performed, at a different position of the movable member (9) along the longitudinal axis (Z) of the token (10).

12. The method according to claim 9 wherein, the movable member (9) not having come into contact with the lateral surface (12a, 12b, 13a, 13b) of the base (11) of the cartography token (10) during a search step, then another search step is performed, at a different position of the movable member (9) along the longitudinal axis (Z) of the token (10).

13. The method according to claim 1, wherein the contact between the movable member (9) and the base (11) or the stud (15) of the token (10) is detected by capacitive measurement.

14. The method according to claim 1, wherein an automaton is used, comprising at least one zone (1, 3) equipped with fixed elements, such as for example specimens, bowls (4) or bottles (2), said zone (1, 3) comprising at least three cartography tokens (10), the positions of at least one point (O) on each cartography token (10) being determined with respect to the movable member (9) by means of steps (a) to (e), the positions of the various fixed elements (2, 4) of the zone (1, 3) being determined by interpolation by means of the positions of the points (O) of the various cartography tokens (10).

15. The method according to claim 14, wherein the zone comprises a plate (1, 3) extending in a plane, housings being provided in said plate (1, 3), the fixed elements (2, 4) being mounted in said housings.

16. The method according to claim 1, wherein an in-vitro diagnosis device is used as the automaton, the movable member being a sampling needle (9) or pipette.

* * * * *